(12) United States Patent
Caples et al.

(10) Patent No.: US 11,288,728 B2
(45) Date of Patent: Mar. 29, 2022

(54) FACILITATED COMPARISON OF GEMSTONES

(71) Applicant: Blue Nile, Inc., Seattle, WA (US)

(72) Inventors: Andrew Caples, Seattle, WA (US); Martin Springer, Seattle, WA (US); Amanda Johns, Seattle, WA (US); Saurabh Verma, Bellevue, WA (US); Andrew Layman, Auburn, WA (US); Akhil Gupta, Everett, WA (US)

(73) Assignee: BLUE NILE, INC., Seattle, WA (US)

( * ) Notice: Subject to any disclaimer, the term of this patent is extended or adjusted under 35 U.S.C. 154(b) by 237 days.

(21) Appl. No.: 16/528,275

(22) Filed: Jul. 31, 2019

(65) Prior Publication Data

US 2021/0035178 A1 Feb. 4, 2021

(51) Int. Cl.
*G06Q 30/06* (2012.01)
*G01N 33/38* (2006.01)

(52) U.S. Cl.
CPC ....... *G06Q 30/0629* (2013.01); *G01N 33/381* (2013.01); *G06Q 30/0627* (2013.01); *G06Q 30/0631* (2013.01); *G06Q 30/0643* (2013.01)

(58) Field of Classification Search
CPC .......... G06Q 30/0643; G06Q 30/0631; G06Q 30/0627; G06Q 30/0629; G01N 33/381
USPC ......................... 705/26.64, 26.7, 26.63, 27.1
See application file for complete search history.

(56) References Cited

U.S. PATENT DOCUMENTS

| | | | | |
|---|---|---|---|---|
| 7,720,720 B1* | 5/2010 | Sharma | ............... | G06Q 30/0631 705/26.7 |
| 8,326,700 B1* | 12/2012 | Laufer | .................. | G06Q 30/00 705/26.64 |
| 9,489,400 B1* | 11/2016 | Haitani | ................... | G06F 16/26 |
| 10,115,146 B1* | 10/2018 | Anderson | ........... | G06Q 30/0631 |
| 10,802,691 B2* | 10/2020 | Ikuta | ..................... | G06F 3/0482 |
| 2003/0208399 A1* | 11/2003 | Basak | .................... | G06Q 30/02 705/14.53 |

(Continued)

FOREIGN PATENT DOCUMENTS

KR 2011/0123006 * 5/2010 ......... G06Q 30/0601

OTHER PUBLICATIONS

Martijn Kagie, Michiel van Wezel, Patrick J.F. Groenen, "A graphical shopping interface based on product attributes," Decision Support Systems, vol. 46, Issue 1, 2008, pp. 265-276, ISSN 0167-9236, (https://www.sciencedirect.com/science/article/pii/S0167923608001255) (Year: 2008).*

*Primary Examiner* — Yogesh C Garg
(74) *Attorney, Agent, or Firm* — Perkins Coie LLP

(57) ABSTRACT

Methods and systems are provided for facilitating comparison of gemstones having multiple attributes that characterize the gemstones. A facilitated comparison system receives from a user a selection of a gemstone in a collection of the gemstones. Each gemstone in the collection is associated with a selling index indicating a probability of the gemstone being bought by a customer. For each of a predetermined set of the attributes, the system determines one or more comparable ranges. The system identifies alternate gemstones to recommend using the comparable ranges for the attributes and the selling indices of the gemstones. The system displays to the user the selected gemstone and one or more of the alternate gemstones for comparison.

19 Claims, 8 Drawing Sheets

(56) References Cited

U.S. PATENT DOCUMENTS

| | | | | |
|---|---|---|---|---|
| 2005/0234753 | A1* | 10/2005 | Pinto | G06Q 30/02 |
| | | | | 700/44 |
| 2008/0082479 | A1* | 4/2008 | Chang | G06Q 30/0629 |
| 2009/0299877 | A1* | 12/2009 | Vadon | G06F 16/242 |
| | | | | 705/26.1 |
| 2009/0327163 | A1* | 12/2009 | Swan | G06Q 30/0283 |
| | | | | 705/400 |
| 2012/0047146 | A1* | 2/2012 | Balakrishnan | G06F 16/34 |
| | | | | 707/748 |
| 2012/0066217 | A1* | 3/2012 | Eder | G06F 16/951 |
| | | | | 707/723 |
| 2013/0124361 | A1* | 5/2013 | Bryson | G06Q 30/0631 |
| | | | | 705/26.7 |
| 2013/0124449 | A1* | 5/2013 | Pinckney | G06F 16/2425 |
| | | | | 706/52 |
| 2014/0052563 | A1* | 2/2014 | Watkins | G06Q 30/0621 |
| | | | | 705/26.5 |
| 2014/0344115 | A1* | 11/2014 | Yatsuda | G06F 16/248 |
| | | | | 705/26.63 |
| 2014/0372414 | A1* | 12/2014 | Malinowski | G06F 16/248 |
| | | | | 707/722 |
| 2016/0027087 | A1* | 1/2016 | Ahmed | G06Q 30/0631 |
| | | | | 705/26.7 |
| 2016/0155254 | A1* | 6/2016 | Briscoe | G06F 3/0485 |
| | | | | 345/467 |
| 2017/0287044 | A1* | 10/2017 | Rose | H04L 67/306 |
| 2019/0205938 | A1* | 7/2019 | Van Winkle | G06Q 30/0269 |
| 2020/0380540 | A1* | 12/2020 | Fox | G06N 20/00 |

* cited by examiner

|  | 801<br>This Diamond | 802 | 803<br>More for your $ | 804<br>Stretch your Budget | 805<br>Best way to Save |
|---|---|---|---|---|---|
| ▶ Play All | ▲ | ▲ | ▲ | ▲ | ▲ |
| Enlarge | ⊕ | ⊕ | ⊕ | ⊕ | ⊕ |
| View Details | LD11526423 | LD11601746 | LD10267284 | LD11147903 | LD10689624 |
| Add to | ADD TO ▶ | ADD TO ▶ | ADD TO ▶ | ADD TO ▶ | ADD TO ▶ |
| Price | $6,847 | $6,107 + | $6,861 | $8,072 - | $6,064 + |
| Carat Weight *i* | 1.00 | 1.00 | 1.00 | 1.17 + | 1.00 |
| Shape *i* | RD | RD | RD | RD | RD |
| Cut *i* | Ideal | Ideal | Ideal | Ideal | Ideal |
| Color *i* | G | G | G | G | G |
| Clarity *i* | VS1 | VVS2 + | VVS1 ++ | VVS1 ++ | VS1 |
| Polish *i* | Excellent | Excellent | Excellent | Excellent | Excellent |
| Symmetry *i* | Very Good | Excellent + | Very Good | Excellent + | Very Good |
| CCCC *i* | None | None | None | None | None |
| Fluorescence *i* | Faint | Strong - | None + | Medium - | Strong - |

FIG. 8

FACILITATED COMPARISON OF GEMSTONES

BACKGROUND

When a consumer purchases a gemstone, they must take into account a large number of attributes that characterize the gemstone. Some attributes play more important roles than others when consumers make purchase decisions. For example, some consumers may be more interested in purchasing gemstones with particular cuts. As another example, some consumers may consider clarity of gemstones to be more important than other attributes such as cut or color. Gemstones have a seemingly unlimited number of possible combinations of attributes. For example, for a 1.00 carat round diamond, there are 10,080 possible combinations of cut, color, clarity, polish, symmetry, and fluorescence. Further, there are multiple strategies for optimizing diamond attributes within a budget depending on consumers' preferences. As a result, making a purchase decision of a gemstone can be confusing and overwhelming for average consumers. Although there are online comparison tools that assist consumers with comparing similar non-unique products (e.g., mobile phones, televisions, etc.), retailers of gemstones have struggled to develop a similar tool for comparing gemstones and providing insightful recommendations, partly because no two gemstones are the same. Therefore, there is a need for a system that facilitates consumers' purchasing process by allowing consumers to easily compare diverse options of gemstones and providing intelligent recommendations that factor in consumers' preferences.

BRIEF DESCRIPTION OF THE DRAWINGS

FIG. 8 is an example gemstone detail page generated by the FCOM system for displaying details of multiple gemstones for comparison in some embodiments.

DETAILED DESCRIPTION

Figure 1:
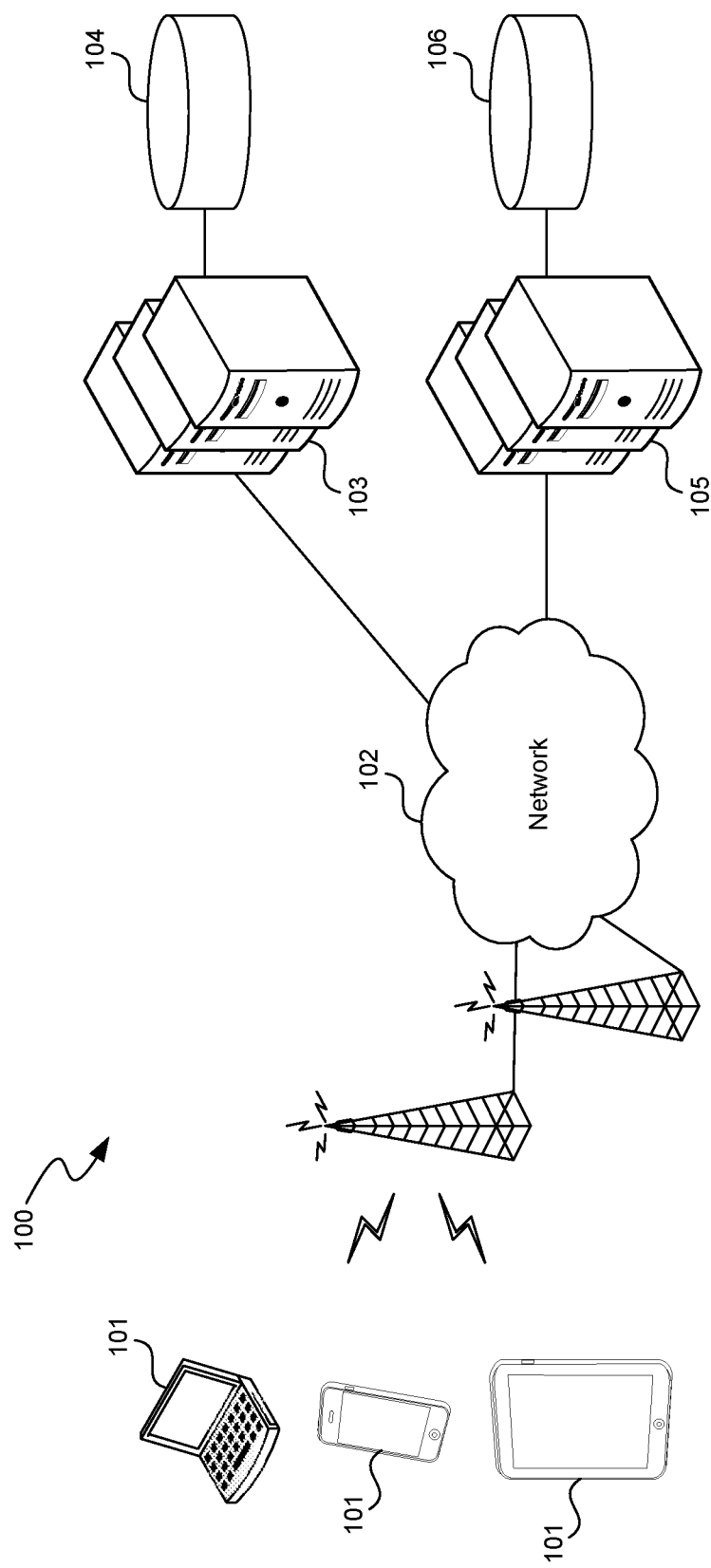
FIG. 1 is a schematic diagram of an environment in which a facilitated comparison (FCOM) system may be implemented in some embodiments.

Methods and systems for facilitating comparison of gemstones having multiple attributes that characterize the gemstones are provided. In some embodiments, a facilitated comparison (FCOM) system receives from a user a selection of a gemstone (e.g., a diamond) in a collection of gemstones of a retailer. Each gemstone has a set of associated attributes, such as, but not limited to, price, weight, cut, color, and clarity. Each gemstone in the collection is also associated with a selling index. The selling index of a gemstone represents a selling probability of the gemstone (i.e., how likely the gemstone will be bought by a customer based on the gemstone's characteristics). When the FCOM system receives the selection, the FCOM system determines comparable ranges for each of a predetermined set of the attributes (e.g., price, weight, cut, color, and clarity). Once the comparable ranges for the attributes are determined, the FCOM system identifies alternate gemstones to recommend using the comparable ranges for the attributes and the selling indices of the gemstones. For example, the FCOM system may identify gemstones that are within the same price range as the selected gemstone and have a color grade one level higher than or equal to, a clarity grade two levels higher than or equal to, and a selling index higher than or equal to the selected gemstone. The FCOM system then displays to the user the selected gemstone and one or more of the alternate gemstones for comparison.

In some embodiments, the FCOM system generates a grid to display the alternate gemstones. The grid has a two-dimensional structure with two axes. For example, the horizontal axis can represent gemstone quality (e.g., "less gemstone," "same gemstone," and "more gemstone"), and the vertical axis can represent gemstone prices (e.g., "lower price," "same price," and "higher price"). Each box of the grid has a set of criteria that specify ranges for the attributes and a range for the selling index. Also, each box may be associated with a descriptive text label that summarizes the one or more most important differences between that box's gemstone and the currently-selected gemstone. For example, a box might be labeled "Best Way to Save" if the box reflects a combination of attributes that represent a comparable gemstone for a lower price than the currently-selected gemstone. As another example, a box identified by the "more gemstone" on the horizontal axis and the "same price" on the vertical axis can be labeled "More for Your Money." In addition to the descriptive label, the FCOM system can also provide a brief explanation for each box, such as "We can save you money and get you a better diamond," "This is the diamond we would recommend if you want to get a little more at the same price point," etc. In this way, the FCOM system can recommend diverse options of gemstones for comparison with different directions in which the user can search. Further, by presenting the alternate gemstones in the form of a grid (e.g., a nine-box grid), the FCOM system can also ensure that only reasonably comparable gemstones are shown to the user, since the alternate gemstones are kept at the same level or an adjacent level (i.e., a single step up or down) in terms of both quality and price.

In some embodiments, not every gemstone will have a recommendation in every box of the grid. For example, as a user zeros in on a unique or rare gemstone on the retailer's website, there will not be alternatives to get more for the same money or save money on a similar gemstone. In some cases, gaps in the retailer's inventory may also cause certain boxes in the grid to remain unpopulated with recommendations.

In some embodiments, when there are multiple gemstones that meet the criteria of a box of the grid, the FCOM system uses the selling index to determine which gemstone to show in the box. For example, the FCOM system may pick the gemstone with the highest selling index to be shown in the box. By displaying the gemstone with the highest selling index, there is a greater likelihood that the gemstone might be purchased by the viewing consumer.

In some embodiments, the FCOM system uses a predictive model based on historical customer interaction data to compute the selling index of a gemstone. The predictive model receives as inputs the gemstone's characteristics and outputs a likelihood (e.g., a percentage) of the gemstone being purchased by a customer. The predictive model is generated using machine learning. The FCOM system initially gathers from a particular time period the customer interaction data relating to one or more of the following: gemstones viewed, gemstones bought, gemstones added to a shopping cart, and gemstones viewed by customers who bought a gemstone in that time period. This data can be maintained in tables of a data warehouse and obtained via database queries (e.g., SQL). Once the customer interaction data is collected, the FCOM system checks the condition of the data for trends, outliers, exceptions, correctness, consistency, missing information, and skewed information, and cleans or corrects any erroneous data, missing values, extreme values, and outliers in the data to improve the data quality. The FCOM system may perform additional preprocessing of the data (e.g., formatting, sampling, normalization, etc.) to further prepare the data.

When the data preparation is complete, the FCOM system splits the prepared data into training data and test data (e.g., in the ratio of 8:2) to evaluate the performance of various classification models (e.g., logical regression, decision tree, naive Bayes, k-nearest neighbors (KNN), gradient boosting machine (GBM), random forest, XGBoost, CatBoost, etc.). The training data is used to train the classification models, and the test data is used to evaluate their accuracy. When partitioning the data, it is important to select non-overlapping subsets of the data for the training data and the test data to ensure proper testing. This process of training a model on one subset of data and validating the model on the other subset is called cross-validation. In some embodiments, multiple rounds of cross-validation are performed using different partitions of the data, and the validation results are combined (e.g., averaged) over the rounds to derive a more accurate estimate of the model's predictive performance. After cross-validating each model, the FCOM system selects the best performing one (e.g., the model that has the best true positive rate without overfitting). In some embodiments, the accuracy of the selected model can be further improved through hyperparameter tuning. A hyperparameter is a parameter whose value is used to control the learning process, as opposed to other parameters whose values are learned.

In some embodiments, the FCOM system provides a selling index calculator. The selling index calculator has multiple GUI elements (e.g., text fields) where a user can enter various characteristics of a gemstone to calculate its selling index. The entered characteristics are fed into the machine learning model to calculate the selling index of the gemstone. For example, the user can enter a gemstone's price, weight, shape, cut, color, clarity, and width, and then the selling index calculator outputs a number indicating the selling probability of the gemstone. Additionally, the selling index calculator may display a list of gemstones having similar characteristics and their selling indices.

In some embodiments, the FCOM system uses a dynamic threshold to determine a comparable range for an attribute of a gemstone. For example, when determining the same price range as a target price, the FCOM system can use a threshold that varies from 4% to 20% depending on the target price. Using a dynamic threshold is advantageous because while a threshold of +/−4% works well for a $5,000 diamond, the same threshold returns almost no results for a $200 diamond. Similarly, the FCOM system can define a lower price range to be, for example, between −10% and a dynamic range of −20% to −40% of the target price, and a higher price range to be, for example, between +10% and a dynamic range of +25% to +45% of the target price.

In some embodiments, the FCOM system generates a gemstone detail page to display details of multiple gemstones for comparison. The gemstone detail page has a number of cards. Each card includes details about a gemstone (e.g., an image of the gemstone, various attributes of the gemstone, etc.). For example, a gemstone detail page can have five cards with the first card including details of the gemstone that the user has selected, the second card including details of the gemstone that has the highest selling index from the first row of a nine-box grid of alternate gemstones, the third card including details of the gemstone that has the highest selling index from the second row of the nine-box grid, the fourth card including details of the gemstone that has the highest selling index from the third row of the nine-box grid, and the fifth card including details of the gemstone that has the highest selling index from the remaining gemstones in the nine-box grid. In addition, each card can include visual cues of how that card's gemstone compares to the gemstone that the user has selected. For example, one of the cards can include a symbol such as "++" or "↑↑" next to clarity to indicate that the gemstone's clarity is two levels higher than that of the gemstone selected by the user, or "−−" or "↓↓" to indicate that the gemstone's clarity is two levels lower than that of the gemstone selected by the user. By presenting cards to a consumer in a side-by-side fashion, the system greatly facilitates the selection of a gemstone for purchase by the consumer.

Various embodiments of the invention will now be described. The following description provides specific details for a thorough understanding and an enabling description of these embodiments. One skilled in the art will understand, however, that the invention may be practiced without many of these details. Additionally, some well-known structures or functions may not be shown or described in detail, so as to avoid unnecessarily obscuring the relevant description of the various embodiments. The terminology used in the description presented below is intended to be interpreted in its broadest reasonable manner, even though it is being used in conjunction with a detailed description of certain specific embodiments of the invention.

FIG. 1 is a schematic diagram of an environment 100 in which the FCOM system may be implemented in some embodiments. The environment 100 can include one or more user computing devices 101, such as personal computers, laptops, tablets, smartphones, and other fixed or mobile computing devices. The environment also includes one or more server computers 103 and 105. The server computers 103 and 105 can access data stores 104 and 106 containing information on gemstones, including historical customer interaction data involving the gemstones. The server computers 103 and 105 communicate with the user computing devices 101 via a network 102. The network 102 can span one or many networks, including the Internet, an intranet, and other public or private data communication networks. The network 102 may include both wired and wireless (e.g., WLAN, WWAN) connections. Based on user input, the user computing devices 101 send selections of gemstones to the server computers 103 and 105. The computing devices 101 may include one or more programs (e.g., a web browser or a dedicated application) that submit the selections to the server computers 103 and 105. When the server computers 103 and 105 receive a selection of a gemstone from a user computing device 101, the server computers 103 and 105 retrieve information about the selected gemstone from the data stores 104 and 106 and provide the retrieved information to the user computing device 101 for display. In addition to the information about the selected gemstone, the server computers 103 and 105 also provide information about similar gemstones for comparison.

Figure 2:
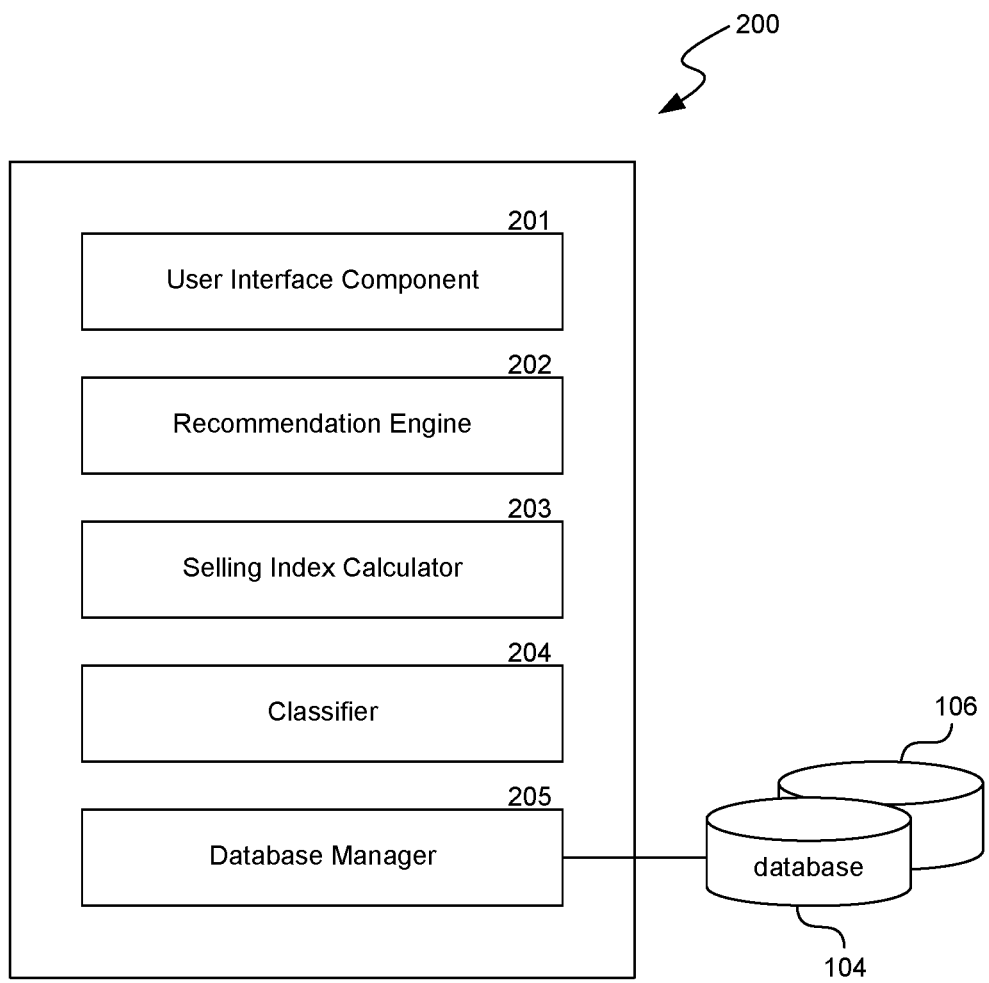
FIG. 2 is a block diagram that illustrates components of the FCOM system in some embodiments.

FIG. 2 is a block diagram that illustrates components of the FCOM system 200 in some embodiments. The FCOM system 200 includes a user interface module 201, a recommendation engine 202, a selling index calculator 203, a classifier 204, and a database manager 205. As will be described in additional detail herein, the user interface module 201 generates GUIs that present information about gemstones, including a recommendation (e.g., nine-box) grid, a gemstone detail page, etc. The recommendation engine 202 provides recommendations and guidance on making purchase decisions of gemstones based on analysis of various customer interaction data, including past purchases, browsing patterns, interests, and preferences of users. In some embodiments, the recommendation engine 202 may also factor in delivery dates when making recommendations. For example, the system may filter identified candidate gemstones to only include those having a delivery availability during a timeframe that is less than or equal to the date on which the target gemstone is available for delivery. The selling index calculator 203 computes the selling index of a gemstone that indicates a probability of the gemstone being purchased by a user. The selling index calculator 203 uses a machine learning classifier 204 to compute the selling index. The classifier 204 receives as in input various attributes of the gemstone and determines the selling index based on analysis of past customer interaction data involving gemstones having similar attributes. The database manager 205 manages access to and maintenance of data stores 104 and 106 that contain information on gemstones. Data in the data stores may be organized in traditional databases or maintained in linked tables, flat files, etc.

The computing systems on which the FCOM system and the other described systems may be implemented may include a central processing unit, input devices, output devices (e.g., display devices and speakers), storage devices (e.g., memory and disk drives), network interfaces, graphics processing units, cellular radio link interfaces, global positioning system devices, and so on. The input devices may include keyboards, pointing devices, touch screens, gesture recognition devices (e.g., for air gestures), head and eye tracking devices, microphones for voice recognition, and so on. The computing systems may include high-performance computing systems, cloud-based servers, desktop computers, laptops, tablets, e-readers, personal digital assistants, smartphones, gaming devices, servers, and so on. The computing systems may access computer-readable media that include computer-readable storage media and data transmission media. The computer-readable storage media are tangible storage means that do not include a transitory, propagating signal. Examples of computer-readable storage media include memory such as primary memory, cache memory, and secondary memory (e.g., DVD) and other storage. The computer-readable storage media may have recorded on them or may be encoded with computer-executable instructions or logic that implements the FCOM system and the other described system modules and/or functionality. The data transmission media are used for transmitting data via transitory, propagating signals or carrier waves (e.g., electromagnetism) via a wired or wireless connection. The computing systems may include a secure cryptoprocessor as part of a central processing unit for generating and securely storing keys and for encrypting and decrypting data using the keys.

The FCOM system and the other described systems may be described in the general context of computer-executable instructions, such as program modules and components, executed by one or more computers, processors, or other devices. Generally, program modules or components include routines, programs, objects, data structures, and so on that perform tasks or implement data types of the FCOM system and the other described modules and/or functionality. Typically, the functionality of the program modules may be combined and operational on a single computing system or distributed across multiple computing systems. Aspects of the FCOM system and the other described systems may be implemented in hardware using, for example, an application-specific integrated circuit ("ASIC") or field programmable gate array ("FPGA").

Figure 3:
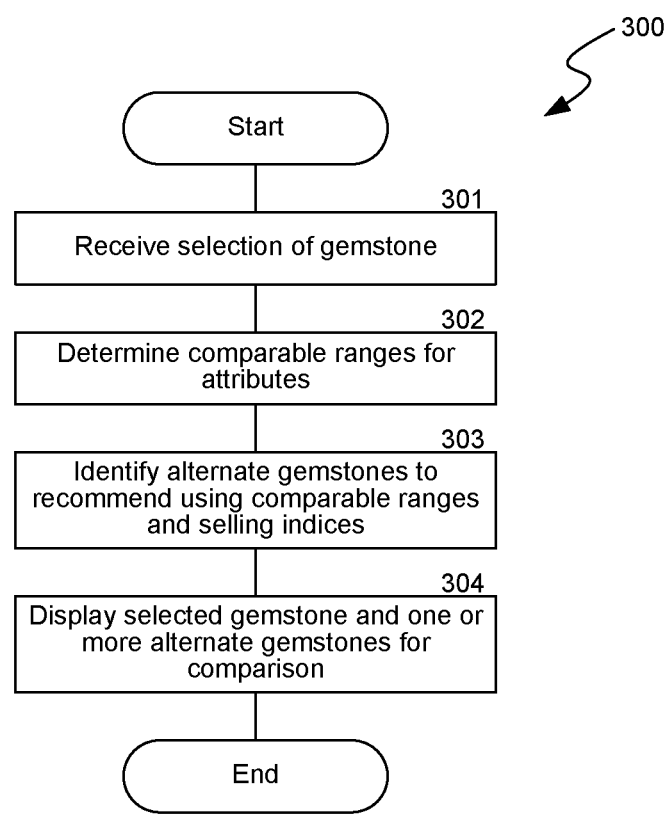
FIG. 3 is a flow diagram that illustrates a method implemented by the FCOM system for recommending alternate gemstones that are similar to a gemstone selected by a user for comparison in some embodiments.

FIG. 3 is a flow diagram that illustrates a method implemented by the FCOM system for recommending alternate gemstones that are similar to a gemstone selected by a user for comparison in some embodiments. In block 301, the method starts by receiving from the user a selection of a gemstone in a collection of gemstones. The user may identify an initial gemstone by browsing within a catalog of gemstones offered for sale or by entering search criteria for a particular gemstone, such as a certain type of gemstone, cut of gemstone, and desired carat weight. In response to a browse action or search request, the FCOM system may identify one or more gemstones that meet the specified criteria. Each gemstone in the collection is associated with a selling index that indicates a selling probability of the gemstone (i.e., how likely the gemstone will be bought by a customer). Once a target gemstone is selected by the user, the FCOM system identifies a set of alternate gemstones to the target gemstone to display to the user. The displayed gemstones are similar to, although not identical with, the target gemstone. To identify the set of alternate gemstones, in block 302 the method determines comparable ranges for each of a predetermined set of attributes that characterize the gemstone (e.g., price, weight, cut, color, and clarity). Typically, the system calculates three values to define the comparable range, namely: (1) the lowest value of the attribute that will be considered equivalent to the target gemstone attribute; (2) a "same" value of the attribute, which although not exactly the same attribute value of the target gemstone, is similar enough that the system treats alternate gemstones having that value as being equal or equivalent to the target gemstone; and (3) the highest value of the attribute that will be considered equivalent to the target gemstone attribute. For example, the method determines a lower price range, the same price range, and a higher price range for the target gemstone. If the target gemstone has a price of $1,000, the lower price range might be calculated as between $900-$995, the same price range as between $995-$1,005, and the higher price range as between $1,005-$1,100. While the lower and higher ranges in this example are each equal in size (i.e., each spans $95 in value), it will be appreciated that the lower and higher ranges may have different sizes.

The calculation of comparable ranges by the system may be performed in a static or dynamic fashion. In some embodiments, the FCOM system uses a static approach for selecting comparable ranges. That is, the FCOM system can search the inventory or catalog of available gemstones for alternate gemstones having attributes that fall within a certain fixed range of the target gemstone attribute. For example, the system may search the dataset of available gemstones in order to identify one or more other gemstones that have attributes that differ from the target gemstone by no more than 1%. Any gemstone having a weight that is within +/−1% of the target gemstone weight may be identified as a candidate gemstone for display to the user.

In some embodiments, the FCOM system uses a dynamic threshold to determine a comparable range for an attribute of a gemstone. The dynamic threshold varies based on the availability/frequency of alternate gemstones at the corresponding attribute value of the target gemstone. For example, higher-priced gemstones may have a broader comparable range around the target gemstone, since the number of available gemstones at higher prices is necessarily limited. In contrast, the number of gemstones at lower prices can be significant, allowing for a narrower comparable range to be applied by the system when searching for alternate gemstones. In some embodiments, the comparable range for pricing can be determined by the system using the following formulas:

$$\text{Same Price} = +/- \left(0.02 + \left(\frac{(P/\tilde{x})^a + (P/\tilde{x})^b}{100}\right)\right) \times P$$

$$\text{Lower Price} =$$

$$\text{Between } 0.9 \times P \text{ AND } \left(.82 - \left(\frac{(P/\tilde{x})^a + (P/\tilde{x})^b}{100}\right)\right) \times P$$

$$\text{Higher Price} = \text{Between } 1.1 \times P \text{ AND } \left(1.23 + \left(\frac{(P/\tilde{x})^a + (P/\tilde{x})^b}{100}\right)\right) \times P$$

where $\tilde{x}$ is the median price of similar gemstones sold recently (e.g., in the past six months), P is the target gemstone price, a is between 0 and −1, and b is between 0 and 1.

In a manner similar to determining comparable price ranges, the FCOM system can apply a similar methodology to assess comparable ranges for other attribute values. As an example, when calculating comparable weight ranges (e.g., lower carat range, same carat range, and higher carat range), the FCOM system may apply the following formulas:

$$\text{Lower Diamond Carat} <= \left(0.03 + \left(\frac{C_w^a + C_w^b}{100}\right)\right) \times C_w$$

$$\text{Same Diamond Carat} = +/- \left(0.03 + \left(\frac{C_w^a + C_w^b}{100}\right)\right) \times C_w$$

$$\text{Higher Diamond Carat} >= \left(0.03 + \left(\frac{C_w^a + C_w^b}{100}\right)\right) \times C_w$$

where $C_w$ is the target carat weight, a is between −1 and −2, and b is between 1 and 2.

In block 303, the method identifies alternate gemstones to recommend using the comparable ranges for the attributes and the selling indices of the gemstones. For example, the method may identify gemstones that are within the same price range as the selected gemstone and have a color grade one level higher than or equal to, a clarity grade two levels higher than or equal to, and a selling index higher than or equal to the selected gemstone. In some embodiments, the method may take into account additional factors such as delivery dates when making the recommendations. For example, the system may filter identified candidate gemstones to only include those having a delivery availability during a timeframe that is less than or equal to the date on which the target gemstone is available for delivery.

In block 304, the method displays the selected gemstone and one or more of the alternate gemstones to the user for comparison and then completes. A methodology implemented by the FCOM system for selecting and displaying certain gemstones is described in additional detail in FIG. 4.

Figure 4:
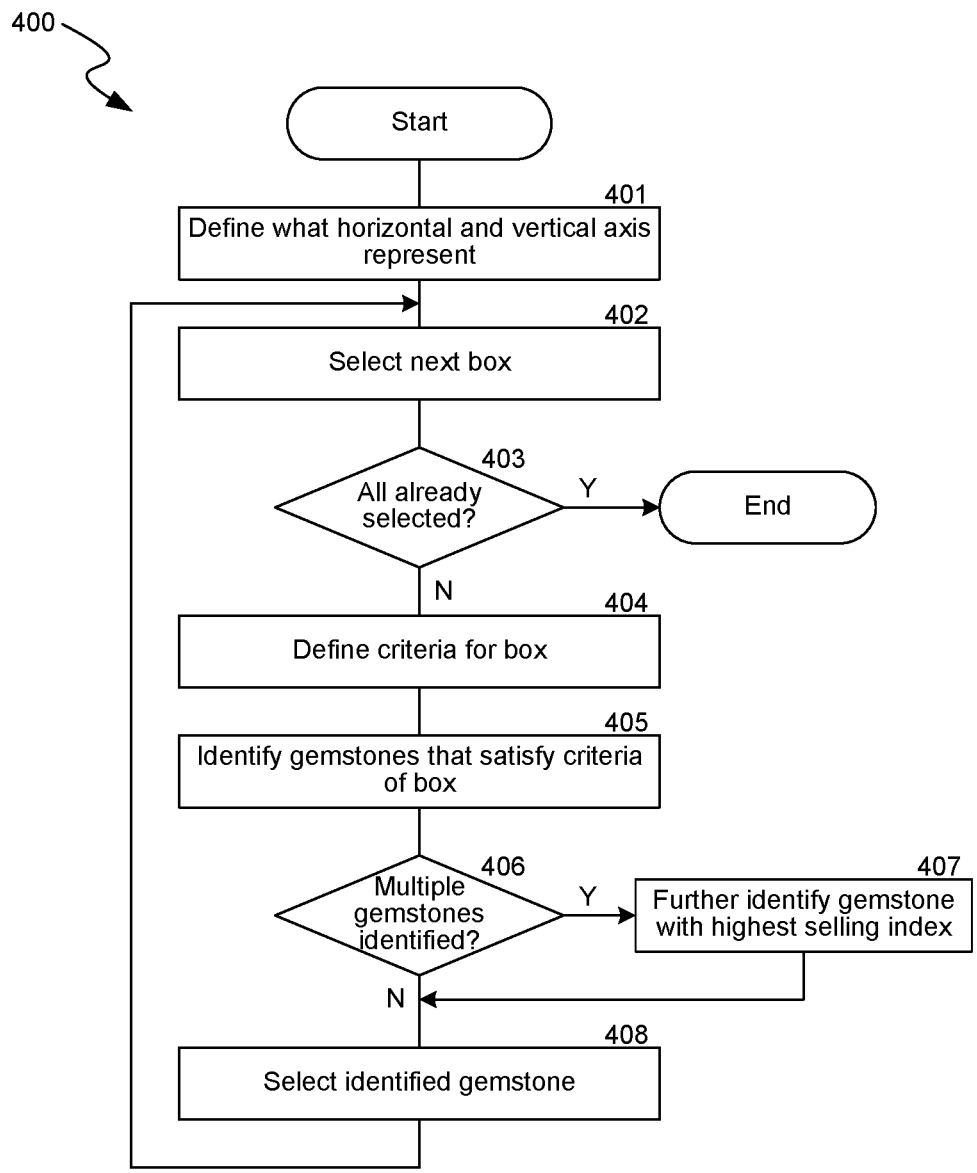
FIG. 4 is a flow diagram that illustrates a method implemented by the FCOM system for generating a nine-box grid to display alternate gemstones that are similar to a target gemstone selected by a user in some embodiments.

FIG. 4 is a flow diagram that illustrates a method implemented by the FCOM system for generating a nine-box grid to display alternate gemstones that are similar to a target gemstone selected by a user in some embodiments. In block 401, the method starts by defining what the horizontal axis and the vertical axis represent. For example, the horizontal axis can represent gemstone quality (e.g., "less gemstone," "same gemstone," and "more gemstone") and the vertical axis can represent gemstone prices (e.g., "lower price," "same price," and "higher price"). In blocks 402-408, the method loops selecting a gemstone to display in each box. In block 402, the method selects the next box in the nine-box grid. In decision block 403, if all the boxes have already been selected, the method completes, else the method continues at block 404. In block 404, the method defines criteria for identifying gemstones for the current box. For example, the criteria can specify ranges for certain attributes (e.g., price, weight, cut, color, and clarity) and a range for the selling index. For example, one box (e.g., the box identified by the "more gemstone" on the horizontal axis and the "lower price" on the vertical axis) can have a set of criteria that specify the following ranges for the attributes and the selling index:

Cut>=Target Cut
    Color>=Target Color−2
    Clarity>=Target Clarity−1
    Selling Index>=Target Selling Index
    Combined Delta>=0

As another example, one box (e.g., the box identified by the "less gemstone" on the horizontal axis and the "same price" on the vertical axis) can have a set of criteria that specify the following ranges for the attributes and the selling index:

Cut<=Target Cut+1
    Color<=Target Color+2
    Clarity<=Target Clarity+1
    Selling Index<=Target Selling Index In block 405, the method identifies gemstones that satisfy the criteria of the current box. In decision block 406, if multiple gemstones are identified that satisfy the criteria of the current box, the method continues at block 407, else the method continues at block 408. In block 407, the method further identifies the gemstone with the highest selling index among the multiple gemstones that were identified in block 405. That is, if there are multiple gemstones that satisfy the criteria of the current box, the system selects the gemstone that is most likely to sell in the next period of time. By displaying gemstones with the highest selling index, the system may be said to present to the user the most commercially viable inventory that is similar to the target gemstone. In block 408, the method selects the identified gemstone and then loops to block 402 to select the next box. If a box has no matching gemstones that satisfy the criteria of the box, no gemstone is displayed in that box. It will be appreciated that by selecting alternative gemstones to the target gemstone in the fashion described above, users are provided with helpful directional data to allow them to more quickly arrive at the gemstone that they wish to purchase.

Figure 5:
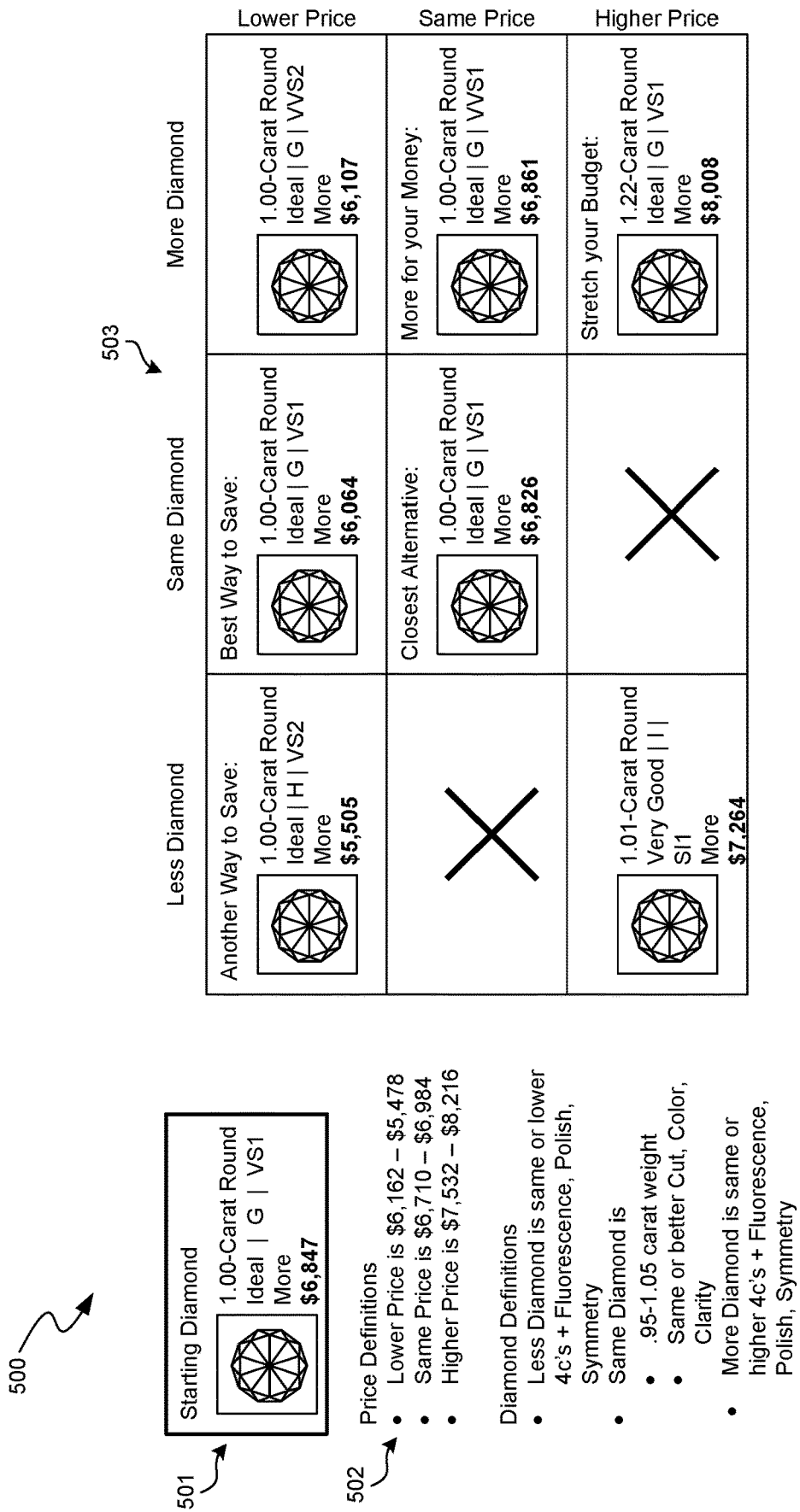
FIG. 5 is an example graphical user interface (GUI) generated by the FCOM system for displaying a target gemstone selected by a user and a nine-box grid of alternate gemstones that are similar to the gemstone selected by the user in some embodiments.

FIG. 5 is an example GUI that is generated by the FCOM system for displaying a target gemstone selected by a user (e.g., a diamond) and a nine-box grid of alternate gemstones that are similar to the gemstone selected by the user. The representative GUI 500 has a region 501 on the upper left side that includes a picture of a diamond selected by the user and various attributes characterizing the diamond, such as its weight, shape, cut, color, clarity, and price. The region 501 also includes a link labeled "More" that the user can click to view more details about the diamond. Below the region 501 is a region 502 displaying price definitions and gemstone definitions. The price definitions specify three different price ranges (lower price, same price, and higher price) comparable to that of the selected diamond. The gemstone definitions specify three different measures of quality (in the depicted case, less diamond, same diamond, and more diamond) based on certain attributes such as carat, cut, color, clarity, fluorescence, polish, and symmetry. The price definitions and the gemstone definitions provide textual support to allow a user to better understand the nine-box grid that is presented to the user on the right side of the GUI 500.

The nine-box grid 503 on the right side of the display presents alternate gemstones to the user. The gemstones are similar, but not identical to, the target gemstone as measured by the different attributes that form the axes of the displayed grid. In the depicted example, the nine-box grid 503 is a table with three rows and three columns. The three rows represent the three price ranges specified by the price definitions, and the three columns represent the three measures of diamond quality specified by the gemstone definitions. Each box includes a diamond that satisfies the criteria of that box. When there are multiple diamonds that satisfy the criteria, the FCOM system may use various criteria to determine which diamond to place in the box. For example, the FCOM system may select the diamond with the highest selling index to be included in that box. Alternatively or additionally, the system may select the diamond with the best shipping availability to display in the box. When there is no diamond that satisfies the criteria of a box, the FCOM either displays an indication to that effect (e.g., an "X" or other graphical or textual treatment that reflects a lack of inventory satisfying the box criteria) or leaves the corresponding box empty. Each box also includes a picture of the diamond, its attributes, a descriptive label, and a link that the user can click to view more details about the diamond. While diamonds are displayed in the GUI 500, it will be appreciated that other gemstones are equally suitable for display in the GUI 500.

While the nine-box grid is one example of the type of interface that is generated by the FCOM system, it will be appreciated that variations could be made to the GUI yet still convey similar information to a user of the system. For example, the size of the grid could be greater than or less than nine boxes. A 3×3 grid has been found in most cases to provide the right amount of information to best guide a user's search, but in other circumstances a larger (e.g., 4×4) or smaller (e.g., 3×2) grid may suffice. Additionally, the grid does not need to be square. Other shapes, such as rectangular or circular displays may also be suitable to convey information to a user. A suitable interface typically has variation along two axes to allow a user to see attribute values both above and below the attributes of the target gemstone.

Figure 6:
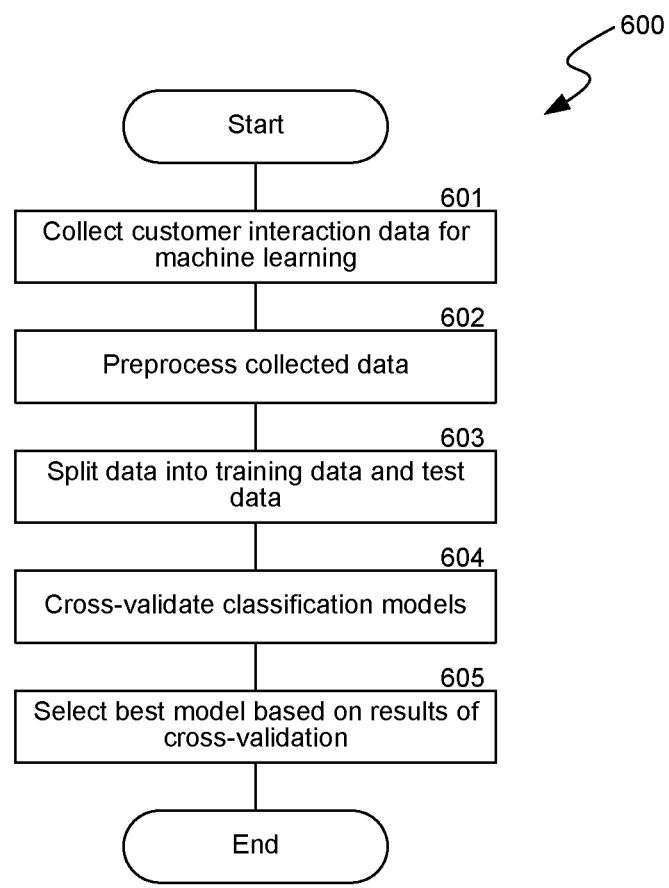
FIG. 6 is a flow diagram that illustrates a method implemented by the FCOM system for selecting a classification model to compute a selling index of a gemstone in some embodiments.

FIG. 6 is a flow diagram that illustrates a method executed by the FCOM system for selecting a classification model to compute a selling index of a gemstone in some embodiments. In block 601, the method starts by collecting customer interaction data from a particular time period (e.g., year 2018). The customer interaction data may include one or more of gemstones viewed, gemstones bought, gemstones added to a shopping cart, and gemstones viewed by customers who bought a gemstone in that time period. In block 602, the method performs preprocessing on the collected data, such as cleaning, formatting, sampling, normalization, etc., to improve the data quality. In block 603, the method splits the data into two datasets: a training dataset and a test dataset. The training dataset is used to train classification models, and the test dataset is used to evaluate the accuracy of the models. In block 604, the method cross-validates the models by fitting the models on the training dataset and validating the fitted models on the test data set. Multiple rounds of cross-validation may be performed using different partitions of the data, and the validation results may be combined (e.g., averaged) over the rounds to derive a more accurate estimate of the model's predictive performance. In block 605, the method selects the best performing model based on the results of the cross-validation. For example, the best performing model may be identified as the one that has the best true positive rate without overfitting. The best performing model takes as input attribute values of a gemstone. Based on those attributes, the best performing model outputs a selling index value that reflects the likelihood that the gemstone will sell within a particular time period. The particular time period during which a gemstone is likely to sell may be equal to the length of historical data being analyzed by the method, or the time period may reflect a subset of that period. For example, even if two years of historical data is analyzed by the method, the selling index may reflect a likelihood that a particular gemstone will sell within 6 months. In one embodiment, the selling index value is a percentage value that ranges between 0.00 and 1.00. For example, a selling index value of 0.95 indicates a gemstone that is likely to sell quickly (i.e., a 95% likelihood of sale within a 6-month period), whereas a selling index value of 0.35 indicates a gemstone is likely to sell slowly (i.e., a 35% chance that the gemstone will sell within a 6-month period). A scaled value of between 0 and 1 is only one example of a selling index value, however. In other embodiments, the model may return a selling index value that reflects a sales quartile (e.g., top 25% selling gemstone, second 25%, third 25%, bottom 25%) or other metric reflective of sales.

The classification model used to generate a selling index value may periodically be retrained using more recent sales data or larger sets of sales data. Particularly in the gemstone market, consumer preferences change over time. In certain years, one type of gemstone may sell particularly well. In other years, that same gemstone may lag in sales. As such, periodic retraining of the classification model is necessary to ensure that the model reflects current consumer purchasing behavior. Additionally, the classification model may be retrained to take into account seasonal, regional, or other differences. For example, the selling indices leading up to Valentine's Day may be different for different types of gemstones or jewelry than the selling indices leading up to Mother's Day. Likewise, regional differences may lead to different selling indices. For example, the selling indices for the U.S. market may be different than the selling indices for the Chinese market. As such, the system may calculate and use different selling indices depending on the time of year, the particular marketplace, and/or other factors which are found to impact sale time.

Figure 7:
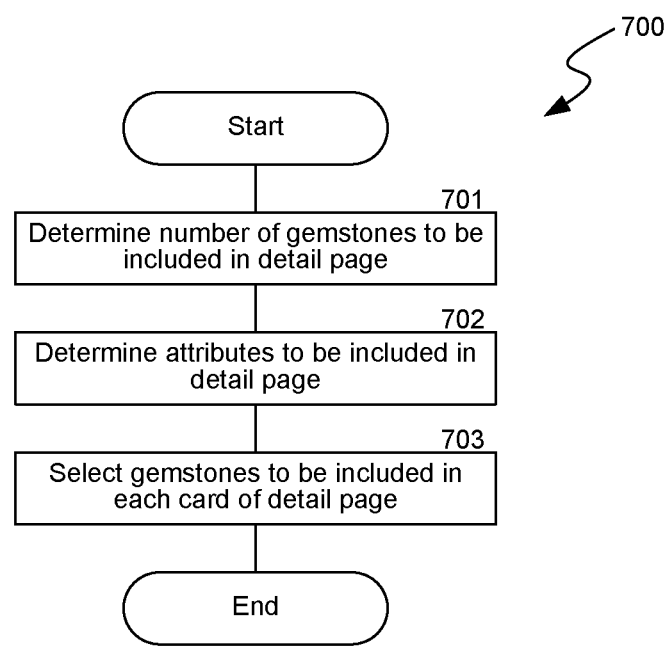
FIG. 7 is a flow diagram that illustrates a method implemented by the FCOM system for generating a gemstone detail page that displays details of multiple gemstones for comparison in some embodiments.

FIG. 7 is a flow diagram that illustrates a method executed by the FCOM system for generating a gemstone detail page that displays details of multiple gemstones for comparison in some embodiments. The gemstone detail page has a number of cards, as depicted in FIG. 8. Each card includes details about a gemstone (e.g., an image of the gemstone, various attributes of the gemstone, etc.). In block 701, the method starts by determining the number of cards/gemstones to be included in the gemstone detail page. The number of cards to display is typically determined by the type of device and size of the user's display. For example, users viewing the gemstone detail page on a mobile device will be presented with less cards than users viewing the gemstone detail page on a tablet, laptop, or desktop computer. In block 702, the method determines which attributes to be included in the gemstone detail page for comparison. For example, the gemstone detail page may include the price, weight, shape, cut, color, clarity, polish, symmetry, culet, and fluorescence for each gemstone. The number of attributes included on a gemstone detail page may be determined by assessing an amount of available display space on a particular UI and selecting a number of attributes that will fit within the available display space. Alternatively or additionally, the method may merely display a fixed number (e.g., 5) of the most commonly-searched attributes in each detail page. In block 703, the method selects gemstones to be included in each card for comparison. Gemstones may be selected using a similar technique as was used to identify alternate gemstones for display in a nine-box grid, as described previously in conjunction with FIGS. 4 and 5. For example, if the gemstone detail page has four cards, the method can select the gemstone that the user has selected, the gemstone that has the highest selling index from the lower price range (as compared to the user-selected gemstone), the gemstone that has the highest selling index from the same prince range as the user-selected gemstone, and the gemstone that has the highest selling index from the higher price range (as compared to the user-selected gemstone).

FIG. 8 is an example gemstone detail page generated by the FCOM system for displaying details of multiple gemstones for comparison in some embodiments. The gemstone detail page 800 includes five cards 801, 802, 803, 804, and 805, each of which can include a different gemstone. For example, card 801 can include a gemstone that the user has selected, card 802 can include the gemstone that has the highest selling index from the first row of a nine-box grid of alternate gemstones, card 803 can include the gemstone that has the highest selling index from the second row of the nine-box grid, card 804 can include the gemstone that has the highest selling index from the third row of the nine-box grid, and card 805 can include the gemstone that has the highest selling index from the remaining gemstones in the nine-box grid. Each card displays an image and various attributes of the gemstone, such as price, carat weight, shape, cut, color, clarity, polish, symmetry, culet, and fluorescence. Next to an attribute, a card can display a visual cue of how that attribute compares to the corresponding attribute of the gemstone that the user has selected. For example, card 802 displays a plus (+) symbol next to clarity to indicate that the gemstone's clarity is one level higher than that of the gemstone selected by the user. Each card also includes options that allow the user to play a 360-degree video of the gemstone, view an enlarged image of the gemstone, view more details of the gemstone, and add the gemstone to a ring, a pendant, or a shopping cart.

An implementation of the FCOM system may employ any combination of the embodiments described above. The processing described above may be performed by a computing system with a processor that executes computer-executable instructions stored on a computer-readable storage medium that implements the FCOM system.

Although the subject matter has been described in language specific to structural features and/or acts, it is to be understood that the subject matter defined in the appended claims is not necessarily limited to the specific features or acts described above. Rather, the specific features and acts described above are disclosed as example forms of implementing the claims. Accordingly, the invention is not limited except as by the appended claims.

We claim:

1. A method performed by one or more computing systems for facilitating comparison of gemstones having multiple attributes that characterize the gemstones, the method comprising:
   receiving from a user a selection of a gemstone in a collection of the gemstones,
      wherein each gemstone in the collection is associated with a selling index indicating a probability of the gemstone being bought by a customer, and
      wherein, for each gemstone in the collection, the selling index is generated by the one or more computing systems using a selling index calculator that applies a machine learning classifier, by accessing at least one attribute of the gemstone and analyzing past customer interaction data for gemstones having similar attributes;
   for each of a predetermined set of the attributes, determining one or more comparable ranges by the one or more computing systems;
   identifying, by the one or more computing systems, alternate gemstones to recommend using the one or more comparable ranges for the attributes; and
   displaying, to the user via a graphical user interface, the selected gemstone and one or more of the alternate gemstones for comparison,
   wherein the one or more alternate gemstones are displayed based on a corresponding selling index, and
   wherein the graphical user interface includes, for at least one of the displayed one or more alternate gemstones, a visual cue associated with an attribute of the alternate gemstone, the visual cue indicating a comparison between the attribute of the alternate gemstone and a corresponding attribute of the selected gemstone.

2. The method of claim 1, wherein the predetermined set of the attributes include a price, a weight, a cut, a color, and clarity.

3. The method of claim 1, further comprising generating a nine-box grid to display one or more of the alternate gemstones for comparison.

4. The method of claim 3, wherein the nine-box grid has a horizontal axis and a vertical axis, wherein the horizontal axis represents measures of gemstone quality and the vertical axis represents gemstone price ranges.

5. The method of claim 3, wherein each box of the nine-box grid has criteria that specify ranges for each of the predetermined set of the attributes and a range for the selling index.

6. The method of claim 5, wherein each box of the nine-box grid is associated with a descriptive label that describes gemstones that satisfy the criteria of the box.

7. The method of claim 5, further comprising when multiple gemstones satisfy the criteria of a box, selecting a gemstone with the highest selling index to be displayed in that box.

8. The method of claim 1, wherein the selling index of a gemstone is computed using a predictive model based on historical customer interaction data.

9. The method of claim 8, wherein the historical customer interaction data relate to one of more of gemstones viewed, gemstones bought, gemstones added to a shopping cart, and gemstones viewed by customers who bought a gemstone in a given time period.

10. The method of claim 8, wherein the predictive model is selected from a number of classification models based on results of cross-validation of the classification models.

11. The method of claim 1, further comprising providing a selling index calculator that inputs one or more of the attributes of a gemstone and outputs a probability that the gemstone will be bought by a customer.

12. The method of claim 11, wherein the selling index calculator outputs selling indices of gemstones having attributes similar to the one or more attributes input by the selling index calculator.

13. The method of claim 1, wherein a comparable range for an attribute is determined using a dynamic threshold that varies with a value of the attribute.

14. The method of claim 1, wherein delivery dates of the gemstones are taken into account when identifying the alternate gemstones.

15. One or more computing systems for facilitating comparison of gemstones having multiple attributes that characterize the gemstones, the one or more computing systems comprising:

one or more non-transitory computer-readable storage mediums storing computer-executable instructions for controlling the one or more computing systems to:
receive from a user a selection of a gemstone in a collection of the gemstones,
wherein each gemstone in the collection is associated with a selling index indicating a probability of the gemstone being bought by a customer, and
wherein, for each gemstone in the collection, the selling index is generated by the one or more computing systems using a selling index calculator that applies a machine learning classifier, by accessing at least one attribute of the gemstone and analyzing past customer interaction data for gemstones having similar attributes;
for each of a predetermined set of the attributes, determine one or more comparable ranges by the one or more computing systems;
identify, by the one or more computing systems, alternate gemstones to recommend using the one or more comparable ranges for the attributes; and
display, to the user via a graphical user interface, the selected gemstone and one or more of the alternate gemstones for comparison,
wherein the one or more alternate gemstones are displayed based on a corresponding selling index, and
wherein the graphical user interface includes, for at least one of the displayed one or more alternate gemstones, a visual cue associated with an attribute of the alternate gemstone, the visual cue indicating a comparison between the attribute of the alternate gemstone and a corresponding attribute of the selected gemstone; and
one or more processors for executing the computer-executable instructions stored in the one or more computer-readable storage mediums.

16. The one or more computing systems of claim 15, wherein the computer-executable instructions further control the one or more computing systems to generate a gemstone detail page to display details of the selected gemstone and at least one of the alternate gemstones for comparison.

17. The one or more computing systems of claim 16, wherein for each gemstone, the gemstone detail page includes options that allow the user to play a 360-degree video of the gemstone, view an enlarged image of the gemstone, view more details of the gemstone, and add the gemstone to a shopping cart.

18. The one or more computing systems of claim 16, wherein the gemstone detail page includes a visual cue next to an attribute of a gemstone to indicate how that gemstone compares to the selected gemstone.

19. The one or more computing systems of claim 15, wherein the computer-executable instructions further control the one or more computing systems to:

generate a nine-box grid that includes one or more of the alternate gemstones for comparison; and generate a gemstone detail page that includes the selected gemstone and a gemstone with the highest selling index from each row of the nine-box grid.

* * * * *